United States Patent [19]

Eckert

[11] 4,407,824

[45] Oct. 4, 1983

[54] PHARMACEUTICAL PREPARATIONS FOR TOPICAL APPLICATION WHICH CONTAIN SALTS OF ALKANECARBOXYLIC ACIDS, NOVEL CARBOXYLIC ACID SALTS AND THE PRODUCTION THEREOF

[75] Inventor: Theodor Eckert, Münster, Fed. Rep. of Germany

[73] Assignee: Ciba-Geigy Corporation, Ardsley, N.Y.

[21] Appl. No.: 236,097

[22] Filed: Feb. 20, 1981

[51] Int. Cl.³ ............................................. A61K 31/14
[52] U.S. Cl. .................................................. 424/329
[58] Field of Search ....................................... 424/329

[56] References Cited

U.S. PATENT DOCUMENTS

| | | | |
|---|---|---|---|
| 3,161,654 | 12/1964 | Shen | 260/319 |
| 3,385,886 | 5/1968 | Nicholson et al. | 260/515 |
| 3,558,690 | 1/1971 | Sallman et al. | 260/471 |
| 3,637,767 | 1/1972 | Alvarez | 260/340 |
| 3,641,040 | 2/1972 | Carney et al. | 260/293.72 |
| 3,641,127 | 2/1972 | Farge et al. | 260/516 |
| 3,647,858 | 3/1972 | Hinkley et al. | 260/470 |
| 3,752,826 | 8/1973 | Carson | 260/326.3 |

*Primary Examiner*—Stanley J. Friedman
*Attorney, Agent, or Firm*—Irving N. Feit

[57] ABSTRACT

The invention relates to pharmaceutical preparations for topical application which contain salts of alkanecarboxylic acids, in particular compounds of the formula

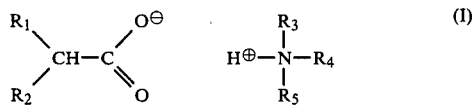

wherein $R_1$ is a group of the formula

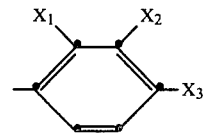

wherein $X_1$ and $X_2$ are hydrogen and $X_3$ is isobutyl, or $X_1$ and $X_3$ are hydrogen and $X_2$ is benzoyl, or $X_1$ is hydrogen, $X_2$ is chlorine, and $X_3$ is 3-pyrrolin-1-yl, or $X_1$ is hydrogen, $X_2$ is a group of the formula —CH=CH—C(OCH$_3$)=CH—$X_4$, and $X_3$ together with $X_4$ are a bond, and $R_2$ is methyl, or $X_2$ and $X_3$ are hydrogen and $X_1$ is 2,6-dichloroanilino, and $R_2$ is hydrogen, or $R_1$ is a group of the formula

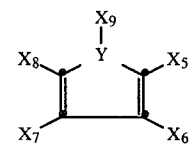

wherein $X_5$ is the common bond with the methine group in formula I, $X_6$ and $X_7$ are hydrogen, $X_8$ is p-methylbenzoyl, Y is a nitrogen atom, and $X_9$ is a methyl group, or $X_5$ is a methyl group, $X_6$ is a common bond with the methine group in formula I, $X_7$ is a group of the formula —CH=C(OCH$_3$)—CH=CH—$X_{10}$, $X_8$ together with $X_{10}$ are a bond, Y is a nitrogen atom and $X_9$ is p-chlorobenzoyl, or $X_5$ is a methyl group, $X_6$ is the common bond with the methine group in formula I, $X_7$ is a group of the formula —CH=C(F)—CH=CH—$X_{11}$, $X_8$ together with $X_{11}$ are a bond, Y is a carbon atom and $X_9$ is (p-methanesulfinylphenyl)methylene, and $R_2$ is hydrogen, and each of $R_3$, $R_4$ and $R_5$ independently is hydrogen, an aliphatic radical, or two of $R_3$, $R_4$ and $R_5$ together are a bivalent aliphatic radical, unsubstituted or substituted or interrupted by aza, oxa or thia, with the proviso that at least one of $R_3$, $R_4$ and $R_5$ is different from hydrogen, optionally in the form of an isomer, together with conventional carriers and/or excipients for topical application. The invention also relates to the production of these preparations and also to novel compounds of the formula I and a process for their production. The compounds of the formula I are suitable for use as anti-inflammatory agents and/or analgesics for topical application.

3 Claims, No Drawings

PHARMACEUTICAL PREPARATIONS FOR TOPICAL APPLICATION WHICH CONTAIN SALTS OF ALKANECARBOXYLIC ACIDS, NOVEL CARBOXYLIC ACID SALTS AND THE PRODUCTION THEREOF

The present invention relates to pharmaceutical preparations for topical application which contain salts of alkanecarboxylic acids, in particular compounds of the formula

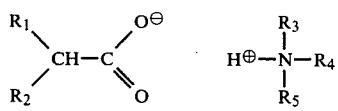

wherein $R_1$ is a group of the formula

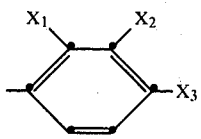

wherein $X_1$ and $X_2$ are hydrogen and $X_3$ is isobutyl, or $X_1$ and $X_3$ are hydrogen and $X_2$ is benzoyl, or $X_1$ is hydrogen, $X_2$ is chlorine, and $X_3$ is 3-pyrrolin-1-yl, or $X_1$ is hydrogen, $X_2$ isa group of the formula $-CH=CH-C(OCH_3)=CH-X_4$, and $X_3$ together with $X_4$ are a bond, and $R_2$ is methyl, or $X_2$ and $X_3$ are hydrogen and $X_1$ is 2,6-dichloroanilino, and $R_2$ is hydrogen, or $R_1$ is a group of the formula

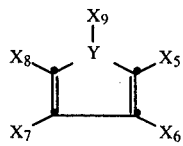

wherein $X_5$ is the common bond with the methine group in formula I, $X_6$ and $X_7$ are hydrogen, $X_8$ is p-methylbenzoyl, Y is a nitrogen atom, and $X_9$ is a methyl group, or $X_5$ is a methyl group, $X_6$ is a common bond with the methine group in formula I, $X_7$ is a group of the formula $-CH=C(OCH_3)-CH=CH-X_{10}$, $X_8$ together with $X_{10}$ are a bond, Y is nitrogen atom and $X_9$ is p-chlorobenzoyl, or $X_5$ is a methyl group, $X_6$ is the common bond with the methine group in formula I, $X_7$ is a group of the formula $-CH=C(F)-CH=CH-X_{11}$, $X_8$ together with $X_{11}$ are a bond, Y is a carbon atom and $X_9$ is (p-methanesulfinylphenyl)methylene, and $R_2$ is hydrogen, and each of $R_3$, $R_4$ and $R_5$ independently is hydrogen, an aliphatic radical, or two of $R_3$, $R_4$ and $R_5$ together are a bivalent aliphatic radical, unsubstituted or substituted or interrupted by aza, oxa or thia, with the proviso that at least one of $R_3$, $R_4$ and $R_5$ is different from hydrogen, optionally in the form of an isomer, together with conventional carriers and/or excipients for topical application, to the use of compounds of the formula I as antiinflammatory agents and/or analgesics for topical application, to novel compounds of the formula I and to the production thereof.

Pharmaceutical preparations for topical application are to be understood as meaning in particular those in which the active ingredient is present in a form in which it can be absorbed by the skin, e.g. together with conventional carriers and/or excipients for topical application.

An aliphatic radical $R_3$, $R_4$ or $R_5$ is preferably a lower alkyl radical which is unsubstituted or substituted by amino, a group of the formula

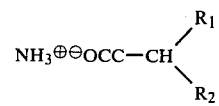

or hydroxyl. Examples of such radicals are lower alkyl, amino-lower alkyl, hydroxyl-lower alkyl, or oligohydroxy-lower alkyl.

A bivalent aliphatic radical is e.g. 4- to 7-membered lower alkylene, whilst a bivalent aliphatic radical which is interrupted by optionally substituted aza, or by oxa or thia, is e.g. 4- to 7-membered 3-aza-, 3-oxa- or 3-thia-lower alkylene, in which aza can be substituted e.g. by lower alkyl.

Throughout this specification, the term "lower" employed to qualify organic radicals and compounds denotes preferably those containing up to and including 7, most preferably up to and including 4, carbon atoms.

The general definitions employed within the scope of this specification have the following preferred meanings:

Lower alkyl is e.g. methyl, ethyl, n-propyl, isopropyl, n-butyl, isobutyl, sec-butyl or tert-butyl, and also comprises corresponding pentyl, hexyl or heptyl radicals.

Amino-lower alkyl is preferably aminomethyl, 2-aminoethyl, 3-aminopropyl or 4-aminobutyl.

Hydroxy-lower alkyl contains in particular a hydroxyl group and is e.g. hydroxymethyl, 2-hydroxymethyl, 2- or 3-hydroxypropyl or 2-, 3- or 4-hydroxybutyl.

Oligo-hydroxy-lower alkyl contains at least two hydroxyl groups and is e.g. 1,2-dihydroxyethyl, 2,3-di- or 1,2,3-trihydroxypropyl, 2,3,4-trihydroxybutyl, 2,3,4,5-tetrahydroxypentyl or, in particular, 2,3,4,5,6-pentahydroxyhexyl derived from D-glucamine, and also di(hydroxymethyl)methyl, tri(hydroxymethyl)methyl or 2-(dihydroxymethyl)ethyl.

Lower alkylene having 4 to 7 members is preferably 1,4-butylene, 1,5-pentylene, 1,6-hexylene, and 1,7-heptylene.

3-Aza-, 3-oxa- or 3-thia-lower alkylene having 4 to 7 members is preferably 3-aza-, 3-N-lower alkyl-aza-, such as 3-N-methyl-aza-, and 3-oxa- or 3-thia-1,5-pentylene, as well as corresponding butylene, hexylene or heptylene.

The compounds of the formula

or the salts thereof, are known. These compounds and their salts with bases are used, for example, as nonsteroidal antiinflammatory agents for treating inflammatory conditions. The preparations containing these compounds are administered for the most part orally and also enterally or parenterally, but in this mode of administration side-effects are observed, especially of a gastro-intestinal nature, for example ulceration of the mucosae of the gastro-intestinal tract. The object of treating different forms of inflammatory diseases, especially of rheumatism of soft tissues, consists in avoiding the side-effects which are primarily connected with systemic therapy. This object is preferably attained by topical therapy if penetration of the active ingredient into the site of the inflammation can be successfully ensured. Successful therapy by percutaneous administration, however, frequently fails when using compounds of the formula (IIIa), because penetration of a therapeutically effective amount of active ingredient through the skin into the affected tissue cannot be adequately ensured.

The present invention is based on the surprising observation that the compounds of the formula (I) possess excellent percutaneous penetration and absorbtion properties.

In addition, the compounds of the formula I have marked anti-inflammatory and analgesic properties. The anti-inflammatory activity can be demonstrated e.g. by the marked reduction in the swelling in rats' paws in the kaolin edema test in accordance with Helv. Physiol. Acta 25, 156 (1967), by rubbing e.g. a gel containing about 0.5 to 5% of active ingredient into the backs of test animals from which the hair has been removed (see Arzneimittel-Forschung 27 (I), 1326, 1977). Further, the anti-inflammatory activity of the active ingredient, e.g. in the form of a gel having a concentration of about 0.5 to 5%, when applied topically, can be deduced from the inhibition of abscess formation induced by subcutaneous injection of carageen in rats (see Arzneimittel-Forschung 27 (I), 1326, 1977).

Assays using compounds of the formula I in the phenyl-p-benzoquinone writhing test (J. Pharmacol. Therap. 125, 237, 1959) in the dosage range from about 1.0 to 120 mg p.o. indicate a marked analgesic activity.

Accordingly, the compounds of the formula I are most suitable anti-inflammatory agents for percutaneous application and can also be used as analgesics.

Accordingly, the invention relates to pharmaceutical preparations for topical application which contain a compound of the formula 1, wherein $R_1$ and $R_2$ are as defined hereinbefore, each of $R_3$, $R_4$ and $R_5$ independently is hydrogen, a lower alkyl radical which is unsubstituted or substituted by amino, a group of the formula

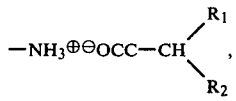

or hydroxyl, or two of $R_3$, $R_4$ and $R_5$ are 4- to 7-membered lower alkylene or 4- to 7-membered lower alkylene which is interrupted by optionally lower alkyl-substituted aza, or by oxa or thia, with the proviso that at least one of $R_3$, $R_4$ and $R_5$ is different from hydrogen, and to the use of these compounds as anti-inflammatory agents and/or analgesics for topical application.

These preparations comprise e.g. pharmaceutical preparations for topical application which contain a compound of the formula I, wherein $R_1$ and $R_2$ have the given meanings, each of $R_3$, $R_4$ and $R_5$ independently is hydrogen, lower alkyl, amino-lower alkyl, lower alkyl substituted by a group of the formula

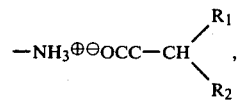

hydroxy-lower alkyl, oligo-hydroxy-lower alkyl, or two of $R_3$, $R_4$ and $R_5$ are 4- to 7-membered lower alkylene or 4- to 7-membered lower alkylene which is interrupted by optionally N-lower alkylated aza, or by oxa or thia.

The invention relates especially to pharmaceutical preparations for topical application which contain a compound of the formula I, wherein $R_1$ and $R_2$ have the given meanings, each of $R_3$, $R_4$ and $R_5$ independently is lower alkyl containing up to and including 4 carbon atoms, such as methyl or ethyl, or hydroxy-lower alkyl containing up to and including 4 carbon atoms, such as 2-hydroxyethyl, or one of $R_3$, $R_4$ and $R_5$ is hydrogen and each of the others independently is lower alkyl containing up to and including 4 carbon atoms, such as ethyl, hydroxy-lower alkyl containing up to and including 4 carbon atoms, such as 2-hydroxyethyl or 2-hydroxypropyl, or together are 4- to 7-membered lower alkylene such as 1,4-butylene or 1,5-pentylene, 4- to 7-membered, optionally N-lower alkylated aza-lower alkylene, or oxa- or thia-lower alkylene, such as 3-aza-, 3-oxa- or 3thia-1,5-pentylene, or one of the others is lower alkyl containing up to and including 4 carbon atoms, such as methyl, and the third is oligohydroxy-lower alkyl such as 2,3,4,5,6-pentahydroxy-1-hexyl which is derived from D-glucamine, or two of $R_3$, $R_4$ and $R_5$ are hydrogen and the other is lower alkyl containing up to and including 4 carbon atoms, such as ethyl, hydroxy-lower alkyl containing up to and including 4 carbon atoms, such as 2-hydroxyethyl, oligo-hydroxy-lower alkyl containing up to and including 4 carbon atoms, such as tris(hydroxymethyl)methyl, amino-lower alkyl containing up to and including 4 carbon atoms, such as 2-aminoethyl, or a group of the formula

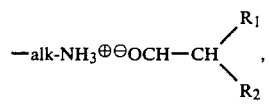

wherein alk is lower alkylene containing up to and including 4 carbon atoms, such as ethylene, and to the use of these compounds as anti-inflammatory agents and/or analgesics for topical application.

The invention relates more especially to pharmaceutical preparations for topical application which contain a compound of the formula I, wherein $R_1$ is a group of the formula IIa, in which $X_1$ is hydrogen, $X_2$ is a group of the formula $-CH=CH-C(OCH_3)=CH-X_4$, and $X_3$ together with $X_4$ are a bond, and $R_2$ is methyl, or $R_1$ is a group of the formula IIa, in which $X_1$ is 2,5-dichloroanilino, $X_2$ and $X_3$ are hydrogen, and $R_2$ is hydrogen, or $R_1$ is a group of the formula IIb, in which $X_5$ is a methyl group, $X_6$ is the common bond with the methine group of the formula I, $X_7$ is a group of the formula $-CH=C(OCH_3)-CH=CH-X_{10}$, $X_8$ together with $X_{10}$ are a bond, Y is a nitrogen atom and $X_9$ is p-chlorobenzoyl, and $R_2$ is hydrogen and $R_3$, $R_4$ and $R_5$ are as just defined above, and to the use of these compounds as anti-inflammatory agents and/or analgesics for topical application.

The invention relates most particularly to pharmaceutical preparations for topical application which contain a compound of the formula I, wherein $R_1$ and $R_2$ have the meanings just given above and $R_3$, $R_4$ and $R_5$ are hydroxy-lower alkyl containing up to and including 4 carbon atoms, such as 2-hydroxyethyl, or one of $R_3$, $R_4$ and $R_5$ is hydrogen and the others are lower alkyl containing up to and including 4 carbon atoms, such as ethyl, hydroxy-lower alkyl containing up to and including 4 carbon atoms, such as 2-hydroxyethyl, or 4- to 7-membered oxa-lower alkylene such as 3-oxa-1,5-pentylene, and to the use of these compounds as anti-inflammatory agents and/or analgesics for topical application.

The invention preferably relates to pharmaceutical preparations for topical application which contain a compound of the formula I, in which $R_1$ is a group of the formula IIa, in which $X_1$ is 2,6-dichloroanilino and $X_2$ and $X_3$ are hydrogen, and $R_2$ is hydrogen, and $R_3$, $R_4$ and $R_5$ are as defined above, and to the use of these compounds as anti-inflammatory agents and/or analgesics for topical application.

Most preferably, the invention relates to pharmaceutical preparations for topical application which contain a compound of the formula I, wherein $R_1$ and $R_2$ are as defined above and one of $R_3$, $R_4$ and $R_5$ is hydrogen and the others are lower alkyl containing up to and including 4 carbon atoms, such as ethyl, or 4- to 7-membered 3-oxa-lower alkylene such as 3-oxa-1,5-pentylene, and to the use of these compounds as anti-inflammatory agents and/or analgesics for topical application.

The invention relates specifically to the pharmaceutical preparations for topical application referred to in the Examples and to the use of these compounds as anti-inflammatory agents and/or analgesics for topical application.

The invention also relates to a process for the production of pharmaceutical preparations for topical application. The process comprises mixing a compound of the formula I with conventional carriers and/or excipients for topical application.

The invention also relates to novel compounds of the formula I, wherein $R_1$ is a group of the formula IIa, in which $X_1$ is hydrogen, $X_2$ is a group of the formula —CH=CH—C(OCH$_3$)=CH—X$_4$, and $X_3$ together with $X_4$ are a bond, $R_2$ is methyl and $R_3$, $R_4$ and $R_5$ are ethyl or 2-hydroxyethyl, or one of $R_3$, $R_4$ and $R_5$ is hydrogen and the others are ethyl, 2-hydroxyethyl or 3-oxa-1,5-pentylene, or $R_1$ is a group of the formula IIa, in which $X_1$ is 2,6-dichloroanilino, $X_2$ and $X_3$ are hydrogen, $R_2$ is hydrogen, and one of $R_3$, $R_4$ and $R_5$ is hydrogen and the others are ethyl, or each of $R_3$, $R_4$ and $R_5$ is hydroxyethyl, or $R_1$ is a group of the formula IIb, in which $X_5$ is methyl, $X_6$ is a common bond with the methine group of the formula I, $X_7$ is a group of the formula —CH=C(OCH$_3$)—CH=CH—X$_{10}$, $X_8$ together with $X_{10}$ are a bond, Y is a nitrogen atom and $X_9$ is p-chlorobenzoyl, $R_2$ is hydrogen, and $R_3$, $R_4$ and $R_5$ are hydroxy-lower alkyl containing up to and including 4 carbon atoms, such as 2-hydroxymethyl, or ethyl, or two of $R_3$, $R_4$ and $R_5$ are hydroxy-lower alkyl containing up to and including 4 carbon atoms, such as 2-hydroxyethyl, or ethyl, and the other is hydrogen, or one of $R_3$, $R_4$ and $R_5$ is hydroxy-lower alkyl containing up to and including 4 carbon atoms, or ethyl, and the others are hydrogen, or an isomer thereof, and to the use thereof, to pharmaceutical preparations containing these compounds, and to a process for their production.

The invention further relates to those novel compounds of the formula I, wherein $R_1$ is a group of the formula IIa, wherein $X_1$ is hydrogen, $X_2$ is a group of the formula —CH=CH—C(OCH$_3$)=CH—X$_4$, and $X_3$ together with $X_4$ are a bond, $R_1$ is methyl and $R_3$, $R_4$ and $R_5$ are ethyl or 2-hydroxyethyl, or one of $R_3$, $R_4$ and $R_5$ is hydrogen and the others are ethyl, 2-hydroxyethyl or 3-oxa-1,5-pentylene.

The invention further particularly relates to those novel compounds of the formula I, wherein $R_1$ is a group of the formula IIa, in which $X_1$ is 2,6-dichloroanilino, $X_2$ and $X_3$ are hydrogen, $R_2$ is hydrogen, and one of $R_3$, $R_4$ and $R_5$ is hydrogen and the others are ethyl, or $R_3$, $R_4$ and $R_5$ are 2-hydroxyethyl.

The invention relates most particularly to those compounds of the formula I, wherein $R_1$ is a group of the formula IIb, in which $X_5$ is methyl, $X_6$ is a common bond with the methine group of the formula I, $X_7$ is a group of the formula —CH=C(OCH$_3$)—CH=CH—X$_{10}$, $X_8$ together with $X_{10}$ are a bond, Y is a nitrogen atom, $X_9$ is p-chlorobenzoyl, $R_2$ is hydrogen and $R_3$, $R_4$ and $R_5$ are hydroxy-lower alkyl containing up to and including 4 carbon atoms, such as 2-hydroxyethyl, or ethyl, or two of $R_3$, $R_4$ and $R_5$ are hydroxy-lower alkyl containing up to and including 4 carbon atoms, such as 2-hydroxyethyl, or ethyl, and the other is hydrogen, or one of $R_3$, $R_4$ and $R_5$ is hydroxy-lower alkyl containing up to and including 4 carbon atoms, such as 2-hydroxyethyl, or ethyl, and the others are hydrogen.

The invention relates specifically to the novel compounds obtained in the Examples and to the methods of preparing them described therein.

Depending on the choice of starting materials and procedures, the compounds of the formula I can be obtained in the form of a possible isomer or of a mixture of isomers, for example optical isomers such as enantiomers or diastereomers, or geometrical isomers such as cis-trans-isomers. The optical isomers are in the form of the pure antipodes and/or racemates. Resultant racemates or mixtures of geometrical isomers can be separated into the pure constituents on the basis of the chemico-physical differences between the components. Thus, for example, racemates of optical antipodes can be resolved into the corresponding antimers by methods which are known per se, e.g. by chromatographic methods, by fractional crystallisation, with micro-organisms or enzymes. Further, it is possible to enrich e.g. optical antipodes by conversion of the other antimer in a racemic mixture. The isomers of novel compounds of the formula I also constitute an object of the invention.

The invention also relates to the production of novel compounds of the formula I, which are obtained by methods which are known per se.

A preferred process variant comprises e.g. reacting an organic carboxylic acid of the formula

or a base salt thereof which is different from a salt of the formula I, with an at least equimolar amount of the amine of the formula

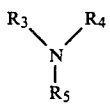

or an acid addition salt thereof, and, if desired, converting a resultant compound of the formula I into another compound of the formula I and/or resolving a resultant mixture of isomers into its individual components.

The molar ratio of acid of the formula (IIIa) and amine of the formula (IIIb) depends on the choice of desired salt or on the number of substituted amino groups in the corresponding compound of the formula (IIIb).

As acid addition salts of amines of the formula (IIIb) there are used e.g. corresponding hydrohalides, such as hydrochlorides.

The reaction of a compound of the formula (IIIa) with a compound of the formula (IIIb) is preferably conducted in an inert solvent or diluent, if necessary with cooling and heating, e.g. in a temperature range from about 0° to 100° C., preferably at room temperature, in a closed vessel and/or in an inert gas atmosphere, e.g. nitrogen.

Examples of suitable solvents and diluents are: water, alcohols such as lower alkanols, e.g. methanol or ethanol, ethers such as di-lower alkyl ethers, e.g. diethyl ether, cyclic ethers such as dioxane or tetrahydrofurane, ketones such as di-lower alkyl ketones, e.g. acetone, carboxylic acid esters such as lower alkanecarboxylic acid esters, e.g. ethyl acetate, amides such as N,N-di-lower alkylamides, e.g. N,N-dimethyl formamide, sulfoxides such as di-lower alkyl sulfoxides, e.g. dimethyl sulfoxide, or mixtures thereof.

The starting materials of the formulae (IIIa) and (IIIb) are known.

The invention also relates to those embodiments of the process in which the starting materials are prepared in situ, or in which a starting material is obtained from a derivative under the reaction conditions and/or is used in the form of a mixture of isomers or of a pure isomer.

The starting materials of the formula (IIIa) can be formed e.g. under the reaction conditions from corresponding esters, such as lower alkyl esters, by hydrolysis in the presence of a base, such as an amine, e.g. dimethylamine. An amine of the formula (IIIb) can be used e.g. in the form of an acid addition salt, such as a halide, e.g. a hydrochloride, and liberated in the presence of a base, such as an amine.

In the process of this invention it is preferred to us those starting materials which lead to particularly useful compounds.

The pharmaceutical preparations of this invention for topical application contain the compounds of the formula I together with a pharmaceutically acceptable carrier or excipient. The daily dosage of the active ingredient depends on the age and individual condition of the patient and also on the mode of application.

Suitable pharmaceutical preparations for topical application are primarily creams, ointments and gels, as well as pastes, foams, tinctures and solutions, which contain from about 0.5 to about 5% of active ingredient.

Creams or lotions are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters; or corresponding ionic emulsifiers, such as alkali metal salts of fatty alcohol sulfates, for example sodium lauryl sulfate, sodium cetyl sulfate or sodium stearyl sulfate, which are customarily used in the presence of fatty alcohols, for example cetyl alcohol or stearyl alcohol. Additives to the aqueous phase include agents which reduce water loss through evaporation, for example polyalcohols, such as glycerol, sorbitol, propylene glycol and/or polyethylene glycols, as well as preservatives, perfumes etc.

Ointments or lotions are water-in-oil emulsions which contain up to 70%, preferably however about 20% to 50%, of water or aqueous phase. The oleaginous phase comprises mainly hydrocarbons, for example petroleum jelly, paraffin oil and/or hard paraffins, which preferably contain hydroxy compounds suitable for improving the water-adsorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase include humectants, such as polyalcohols, for example glycerol, propylene glycol, sorbitol and/or polyethylene glycol, and preservatives, perfuumes etc.

Microemulsions are isotropic systems based on the following four components: water, an emulsifier such as a surfactant, e.g. Eumulgin ®, a lipid such as a non-polar oil, e.g. paraffin oil, and an alcohol containing a lipophilic group, e.g. 2-octyldodecanol. If desired, other ingredients can be added to the microemulsions.

Greasy ointments are anhydrous and contain as base in particular hydrocarbons, for example paraffin, petroleum jelly and/or liquid paraffins, and also natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-adsorption mentioned in connection with the ointments.

In the case of gels a distinction is made between aqueous gels, anhydrous gels, and gels having a low water content, and which consists of swellable gel-forming materials. Primarily transparent hydrogels based on inorganic or organic macromolecules are used. High molecular inorganic components with gel-forming properties are chiefly water-containing silicates such as aluminium silicates, e.g. bentonite, magnesium aluminium silicates, e.g. veegum, or colloidal silica, e.g. aerosil. As high molecular organic substances there are used e.g. natural, semi-synthetic or synthetic macromolecules. Natural and semi-synthetic polymers are derived e.g. from polysaccharides with carbohydrate components of the most widely different kind, such as celluloses, starches, tragacanth, gum arabic, agar-agar, gelatin, alginic acid and salts thereof, e.g. sodium alginate, and their derivatives such as lower alkyl celluloses, e.g. methyl or ethyl cellulose, carboxy- or hydroxy-lower alkyl cellulose, e.g. carboxymethyl cellulose or hydroxyethyl cellulose. The components of synthetic gel-forming macromolecules are e.g. correspondingly substituted unsaturated aliphatics such as vinyl alcohol, vinyl pyrrolidine, acrylic or methacrylic acid. Examples of such polymers are polyvinyl alcohol derivatives such as polyviol, polyvinyl pyrrolidines such as collidone, polyacrylates and polymethacrylates such as Rohagit S ® or Eudispert ®. Conventional additives such as preservatives or perfumes can be added to the gels.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons, such as chlorofluoro-lower alkanes, for example dichlorodifluoromethane and dichlorotetrafluoroethane, being used as propellants. For the oleaginous phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of those emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restorative substances, e.g. fatty acid esters with lower polyethylene glycols, i.e. lipophilic substances which are soluble in the aqueous mixture as substitute for fatty substances which are removed from the skin by the ethanol, and, if necessary, other assistants and additives.

The pharmaceutical preparations for topical application are obtained in known manner, for example by dissolving or suspending the active ingredient in the base or in a part thereof, if necessary. When processing the active ingredient in the form of a solution, it is usually dissolved in one of the two phases before the emulsification, and when processing the active ingredient in the form of a suspension, it is mixed with a part of the base before the emulsification and than added to the remainder of the formulation.

The invention also relates to the use of the novel compounds of the formula I as anti-inflammatory agents for percutaneous application and/or as analgesics, preferably in the form of suitable pharmaceutical preparations.

The following Examples illustrate the invention but in no way limit the scope thereof.

EXAMPLE 1

To a solution of 2 g of 2-(2,6-dichloroanilino)phenylacetic acid in 40 ml of ether are added 2 ml of diethylamine. The solution is refluxed for 10 minutes, then cooled and concentrated under reduced pressure, whereupon diethylammonium-2-(2,6-dichloroanilino)phenylacetate crystallises out. The colourless crystals are isolated by filtration (m.p. 110°–115° C. with decompos.) and dried at room temperature in a high vacuum.

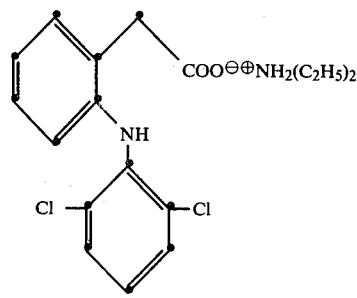

The following compounds are obtained in analogous manner: diethylammonium-[2-(6-methoxy-2-naphthyl)]-propionate with a melting point of 72°–83° C. (decompos.), starting from diethylamine and 2-(6-methoxy-2-naphthyl)propionic acid; diethylammonium-[1-(p-chlorobenzoyl)-5-methoxy-2-methyl-3-indolyl]-acetate with a melting point of 98°–125° C. (decompos.), starting from diethylamine and [1-(p-chlorobenzoyl)-5-methoxy-2-methyl-3-indolyl]-acetic acid.

EXAMPLE 2

With efficient stirring, a solution of 4.53 g of tris(hydroxymethyl)methylamine in 10 ml of water is added dropwise at room temperature and in the course of 10 minutes to a solution of 10 g of 2-(2,6-dichloroanilino)phenylacetic acid in 230 ml of ethyl acetate, whereupon a salt immediately precipitates. The batch is subsequently stirred for half an hour at room temperature and the solvent is removed by rotary evaporation. The white crystalline residue is dissolved in 1 liter of acetone/water (1:1) at about 50° C. The hot solution is concentrated in a rotary evaporator until the first crystals precipitate. The residue is left to crystallise at 0° C., and the precipitated white flocculent crystals are collected on a suction filter and dried in a high vacuum. The resultant tris-(hydroxymethyl)methylammonium-2-(2,6-dichloroanilino)phenylacetate has a melting point of 202°–204° C.

EXAMPLE 3

With efficient stirring, a solution of 5.52 g of triethananolamine in 30 ml of ethyl acetate is added dropwise at room temperature and in the course of 10 minutes to a solution of 10 g of 2-(2,6-dichloroanilino)phenylacetic acid in 230 ml or ethyl acetate, whereupon a salt precipitates immediately. The batch is subsequently stirred for about half an hour at room temperature and the solvent is removed in a rotary evaporator. The white crystalline residue is dissolved in a small amount of hot ethanol and crystallised at 0° C. The white crystals are filtered with suction and dried in a high vacuum. The so obtained triethanolammonium-2-(2,6-dichloroanilino)phenylacetate melts at 137°–138° C.

EXAMPLE 4

With efficient stirring, a suspension of 3.89 g of diethanolamine in 30 ml of ethyl acetate is added dropwise at room temperature and in the course of 10 minutes to a solution of 10 g of 2-(2,6-dichloroanilino)phenylacetic acid in 230 ml of ethyl acetate, whereupon a salt precipitates immediately. The batch is subsequently stirred for half an hour at room temperature and the solvent is removed in a rotary evaporator. The yellowish crystalline residue is dissolved in a small amount of boiling ethanol. The solution is left to stand at 0° C. and diethanolammonium-2-(2,-dichloroanilino)-phenylacetate with a melting point of 130°–132° C. crystallises out.

EXAMPLE 5

With efficient stirring, 3.22 g of morpholine in 30 ml of ethyl acetate are added dropwise at room temperature and in the course of 10 minutes to a solution of 10 g of 2-(2,6-dichloroanilino)phenylacetic acid in 230 ml of ethyl acetate. A salt precipitates about 10 minutes after addition of the morpholine. The batch is then stirred for 1 hour at room temperature and the solvent is removed by rotary evaporation. The white crystalline precipitate is dissolved in boiling ethanol. Morpholinium-2-(2,6-dichloroanilino)-phenylacetate with a melting point of 162°–165° C. crystallises out at 0° C.

The following compounds are obtained in analogous manner: morpholinium-[2-(6-methoxy-2-naphthyl)]-propionate, starting from morpholine and 2-(6-methoxy-2-naphthyl)propionic acid; morpholinium-[1-(p-chlorobenzoyl)-5-methoxy-2-methyl-3-indolyl]-acetate, starting from morpholine and [1-(p-chlorobenzoyl)-5-methoxy-2-methyl-3-indolyl]acetic acid.

EXAMPLE 6

With efficient stirring, 4.93 g of diisopropanolamine in 30 ml of ethyl acetate are added dropwise at room temperature and in the course of 5 minutes to a solution of 10 g of 2-(2,6-dichloroanilino)phenylacetic acid in 230 ml of ethyl acetate. A salt precipitates after a short time. The batch is stirred for 1 hour and the solvent is removed by rotary evaporation. The white crystalline precipitate is dissolved in a small amount of hot ethanol and the solution is left to stand at 0° C., whereupon diisopropanolammonium-2-(2,6-dichloroanilino)phenylacetate with a melting point of 165°–170° C. crystallises out.

EXAMPLE 7

A suspension of 6.64 g of N-methyl-D-glucamine in 100 ml of ethanol together with 10 g of 2-(2,6-dichloroanilino)phenylacetic acid in 230 ml of ethyl acetate are stirred at room temperature overnight under nitrogen. Fine, white crystals precipitate after 2 hours. The solvent is then removed by rotary evaporation and the white tacky residue is dissolved in a small amount of hot water. The clear solution is slowly cooled to 0° C. and left to stand overnight at 0° C. The oily, semi-crystalline precipitate obtained is collected over 2 days on a celite and cloth filter. The filter cake is dried for a week at 60° C./100 mm Hg and then pulverised. The so obtained N-methyl-D-glucammonium-2-(2,6-dichloroanilino)-phenylacetate melts at 127°–130° C.

EXAMPLE 8

An ointment containing 5% of diethylammonium-2-(2,6-dichloroanilino)phenylacetate is prepared as follows:

| Composition | |
|---|---|
| propylene glycol | 10–44% |
| high molecular polyalkylene glycol | 10% |
| viscous paraffin oil | 12% |
| white vaseline | 22% |
| microcrystalline wax | 7% |
| glycerol | 0–34% |
| parabenes | 0.2% |
| active ingredient | 5% |

The active ingredient is dissolved in a mixture of glycerol and propylene glycol and the other components are fused together. The active ingredient solution is then emulsified into the oleaginous phase. If desired, perfume (0.1%) is added after the mixture has been stirred cold.

An ointment containing 0.5% or 2% is prepared in similar manner.

EXAMPLE 9

A transparent hydrogel containing 5% of diethylammonium-2-(2,6-dichloroanilino)phenylacetate is prepared as follows:

| Composition | |
|---|---|
| active ingredient | 5% |
| propylene glycol | 10–20% |
| isopropanol | 20% |
| hydroxypropylmethyl cellulose | 2% |
| water to make up | 100% |

The hydroxypropylmethyl cellulose is swelled in water and the active ingredient is dissolved in a mixture of isopropanol and propylene glycol. The active ingredient solution is then mixed with the cellulose derivative and, if desired, perfume (0.1%) is added. A gel containing 0.5% or 2% of active ingredient is prepared in similar manner.

EXAMPLE 10

A transparent hydrogel containing 5% of diethylammonium 2-(2,6-dichloroanilino)phenylacetate is prepared as follows:

| Composition | |
|---|---|
| active ingredient | 5% |
| propylene glycol | 20% |
| isopropanol | 20% |
| acrylic acid polymer | 2% |
| triethanolamine | 3% |
| water to make up | 100% |

The acrylic acid polymer and water are dispersed and neutralised with triethanolamine. The active ingredient is dissolved in a mixture of isopropanol and propylene glycol. The active ingredient solution is then mixed with the gel. If desired, perfume (0.1%) can be added.

A gel containing 0.5% or 2% of active ingredient can be prepared in similar manner.

EXAMPLE 11

A transparent microemulsion containing 5% of diethylammonium 2-(2,6-dichloroanilino)phenylacetate is prepared as follows:

| Composition | |
|---|---|
| active ingredient | 5% |
| cetyl stearyl alcohol | 27% |
| polyol fatty acid ester | 15% |

| Composition | |
|---|---|
| glycerol | 4% |
| water to make up | 100% |

The cetyl stearyl alcohol and polyol fatty acid ester are heated to 95° C. and the active ingredient is dissolved therein. A mixture of water and glycerol, which has been heated to 95° C., is added. If desired, 0.2% of preservative is added. The resultant microemulsion is cooled, with stirring, and perfume (0.1%) is added, if desired. Transparent emulsions containing 0.5% or 2% of active ingredient are prepared in similar manner.

EXAMPLE 12

A lotion containing 5% of diethylammonium-2-(2,6-dichloroanilino)phenylacetate is prepared as follows:

| Composition | |
|---|---|
| active ingredient | 5% |
| mono- and diglycerides of higher saturated fatty acids with potassium stearate | 8% |
| polyoxyethylene cetyl stearyl ether | 2% |
| decyl oleate | 5% |
| propylene glycol | 20% |
| parabenes | 0.2% |
| demineralized water to make up | 100% |

The active ingredient and the parabenes are dissolved in water and propylene glycol. Then polyoxyethylene cetyl stearyl ether is added to the above solution. Decyl oleate and the glycerides of fatty acids with potassium stearate are fused together and emulsified into the aqueous phase. The lotion is stirred cold and, if desired, perfume (0.1%) is added.

EXAMPLE 13

A solution containing 5% of diethylammonium-2-(2,6-dichloroanilino)phenylacetate is prepared as follows:

| Composition | |
|---|---|
| active ingredient | 5% |
| polyoxyethylene sorbitan fatty acid ester | 10% |
| ethanol | 20% |
| triglyceride (liquid) | 65% |

The active ingredient is dissolved in ethanol and the polyoxyethylene sorbitan fatty acid ester is dissolved in liquid triglyceride. The two solutions are combined and, if desired, perfume (0.1%) is added.

Solutions containing 0.5% and 2% respectively of active ingredient are prepared in similar manner.

EXAMPLE 14

An ointment containing 5% of diethylammonium-2-(2,6-dichloroanilino)phenylacetate is prepared as follows:

| Composition | |
|---|---|
| active ingredient | 5% |
| mono- and diglycerides of higher saturated fatty acids with potassium stearate | 17% |
| decyl oleate | 5% |
| propylene glycol | 20% |
| demineralised water to make up | 100% |

The active ingredient is dissolved in propylene glycol and water. Mono- and diglycerides of saturated fatty acids with potassium stearate are fused together with decyl oleate. The aqueous phase is then added to the oleaginous phase and emulsified. If desired, perfume (0.1%) is added.

A cream containing 0.5% and 2% respectively of active ingredient is prepared in similar manner.

EXAMPLE 15

An ointment containing 5% of diethylammonium 2-(2,6-dichloroanilino)phenylacetate is prepared as follows:

| Composition | |
|---|---|
| active ingredient | 5% |
| propylene glycol | 12% |
| vaseline, white | 28% |
| wax (microcrystalline) | 2% |
| sorbitan fatty acid ester | 25% |
| demineralised water to make up | 100% |

The active ingredient is dissolved in propylene glycol and water. The vaseline, wax and sorbitan fatty acid esters are fused together. The active ingredient solution is then emulsified into the oleaginous phase and, if desired, perfume (0.1%) is added.

An ointment containing 0.5% and 2% respectively of active ingredient is prepared in similar manner.

EXAMPLE 16

A lotion containing 2% of diethylammonium 2-(2,6-dichloroanilino)phenylacetate is prepared as follows:

| Composition | |
|---|---|
| active ingredient | 2% |
| high molecular polyalkylene glycol | 14% |
| liquid triglyceride | 5% |
| viscous paraffin oil | 13% |
| glycerol sorbitan fatty acid ester | 10% |
| demineralised water to make up | 100% |

The active ingredient is dissolved in polyalkylene glycol and water. Triglyceride, paraffin oil and glycerol sorbitan fatty acid ester are fused together. The aqueous phase is then emulsified into the oleaginous phase and, if desired, perfume (0.1%) is added. A lotion containing 0.5% of active ingredient is prepared in similar manner.

Ointments, creams, gels, microemulsions, lotions and solutions containing 0.5%, 2% or 5% of the compounds of Examples 1 to 7 are prepared in the same way as in Examples 8 to 16.

What is claimed is:

1. A method for the treatment of inflammatory and/or painful symptoms in warmblooded organisms which comprises topically administering to such organisms an anti-inflammatory and/or analgesic effective amount of an active compound of the formula I

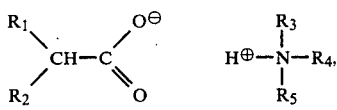 (I)

wherein $R_1$ is a group of the formula

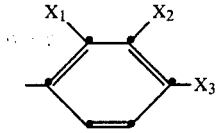 (IIa)

and wherein $X_2$ and $X_3$ are hydrogen; $X_1$ is 2,6-dichloroanilino; $R_2$ is hydrogen;

$R_3$, $R_4$ and $R_5$ are hydroxy-lower alkyl containing up to and including 4 carbon atoms, or one of $R_3$, $R_4$ and $R_5$ is hydrogen and the others are lower alkyl containing up to and including 4 carbon atoms, hydroxy-lower alkyl containing up to and including 4 carbon atoms, or are members of a 2-morpholinium ring, together with pharmaceutically usable conventional carriers and excipients for topical application.

2. A method for the treatment of inflammatory and/or painful symptoms in warmblooded organisms which comprises topically administering to such organisms an anti-inflammatory and/or analgesic effective amount of an active compound of the formula I

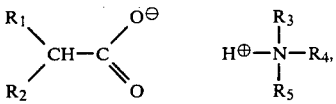 (I)

wherein $R_1$ is a group of the formula

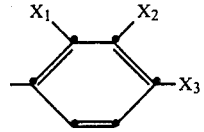 (IIa)

wherein $X_1$ is hydrogen, $X_2$ is chlorine, and $X_3$ is 3-pyrrolin-1-yl; $R_2$ is methyl; and $R_3$, $R_4$ and $R_5$ are hydroxy-lower alkyl containing up to and including 4 carbon atoms; or one of $R_3$, $R_4$, and $R_5$ is hydrogen and the others are lower alkyl containing up to and including 4 carbon atoms, hydroxy-lower alkyl containing up to and including 4 carbon atoms, or are members of a morpholinium ring, together with pharmaceutically usable conventional carriers and excipients for topical application.

3. A method for the treatment of imflammatory and/or painful symptoms in warm-blooded organisms which comprises topically administering to such organisms an anti-inflammatory and/or analgesic effective amount of N-methyl-D-glucammonium-2-(2,6-dichloroanilino)phenylacetate.

* * * * *